United States Patent [19]

Michaelson

[11] Patent Number: 4,691,073
[45] Date of Patent: Sep. 1, 1987

[54] PRODUCTION OF TERTIARY OLEFINS
[75] Inventor: Robert C. Michaelson, Kinnelon, N.J.
[73] Assignee: Exxon Chemical Patents Inc., Linden, N.J.
[21] Appl. No.: 885,529
[22] Filed: Jul. 14, 1986
[51] Int. Cl.$^4$ .............................................. C07C 1/20
[52] U.S. Cl. .................................................. 585/639
[58] Field of Search ........................ 585/640, 639, 638
[56] References Cited

U.S. PATENT DOCUMENTS

| | | | |
|---|---|---|---|
| 3,637,889 | 1/1982 | Watanabe et al. | 260/682 |
| 4,320,232 | 3/1982 | Volkamer et al. | 568/697 |
| 4,343,959 | 8/1982 | Kida et al. | 585/640 |
| 4,398,051 | 8/1983 | Araki et al. | 585/639 |
| 4,524,290 | 3/1981 | Chambers et al. | 568/866 |

FOREIGN PATENT DOCUMENTS

| | | | |
|---|---|---|---|
| 118085 | 2/1983 | European Pat. Off. | 585/639 |
| 0116340 | 2/1983 | European Pat. Off. | 585/639 |
| 3509292 | 3/1985 | Fed. Rep. of Germany | 585/639 |
| 8083635 | 11/1981 | Japan | 585/639 |
| 9013734 | 7/1982 | Japan | 585/640 |
| 9055837 | 9/1982 | Japan | 585/640 |
| 1173128 | 3/1969 | United Kingdom . | |

OTHER PUBLICATIONS

W. D. Keller, "Clays (Survey)", *Kirk–Othmer Encyclopedia of Chemical Technology*, Third Edition, vol. 6, 1979, pp. 190–207, John Wiley & Sons (New York).

*Primary Examiner*—Asok Pal
*Attorney, Agent, or Firm*—F. A. Sinnock; E. T. Wheelock

[57] ABSTRACT

High purity tertiary olefins are obtained in extremely high yields over a sustained period by cracking alkyl tert-alkyl ethers over clay catalysts which have been treated with HF and/or HCl. Preferably temperature are 100°–250° C., the surface area of the catalyst is above 40 $M^2$/gm and the cracking step is part of a process for recovering isobutylene or isoamylene from steam cracked streams.

12 Claims, 4 Drawing Figures

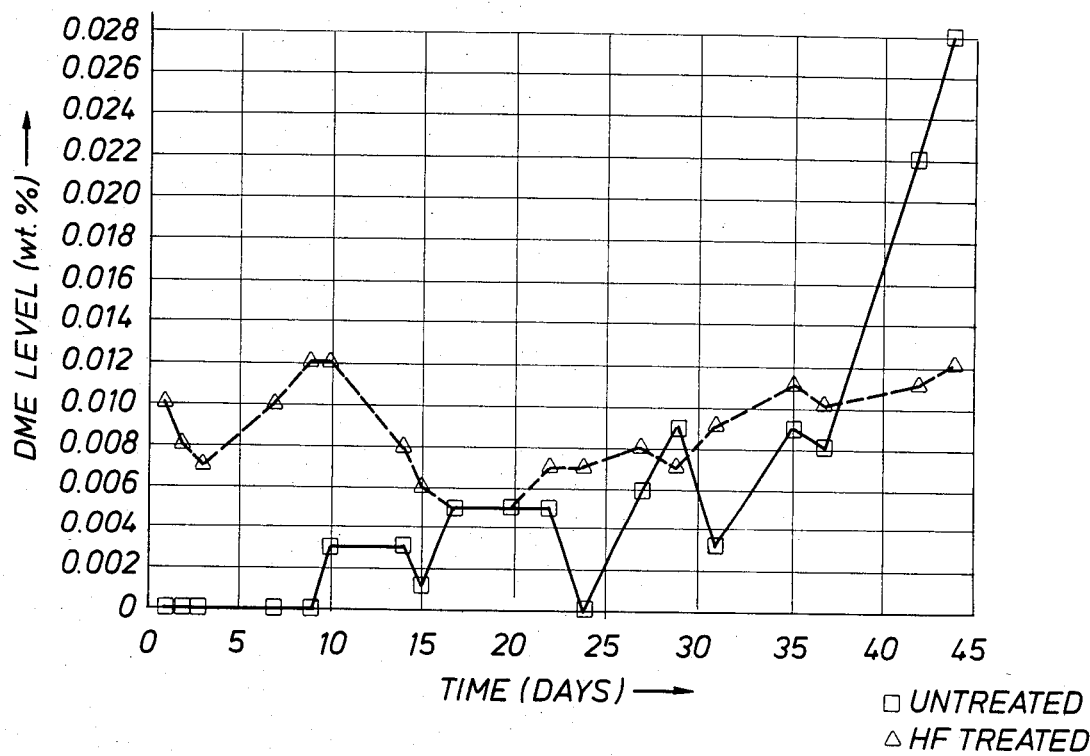
FIG.1A DME LEVELS IN CRACKER PRODUCT UNTREATED CLAY vs. HF TREATED CLAY
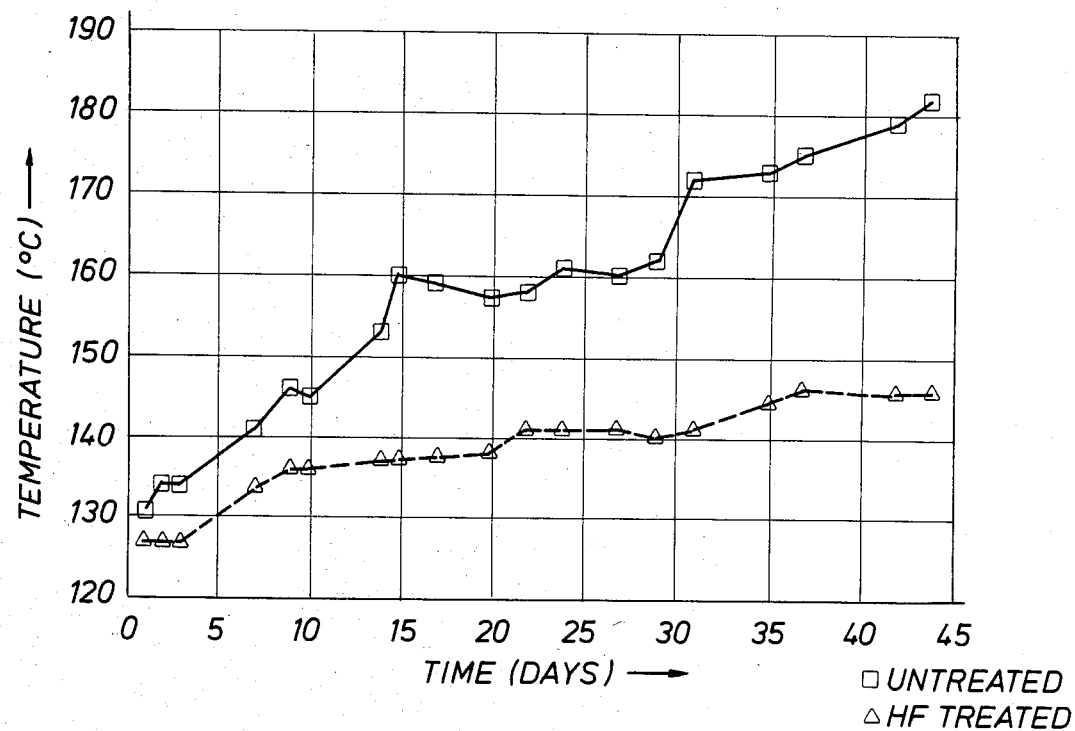
FIG.1B 95% TAME CRACKING LIFE TESTS UNTREATED CLAY vs. HF TREATED CLAY

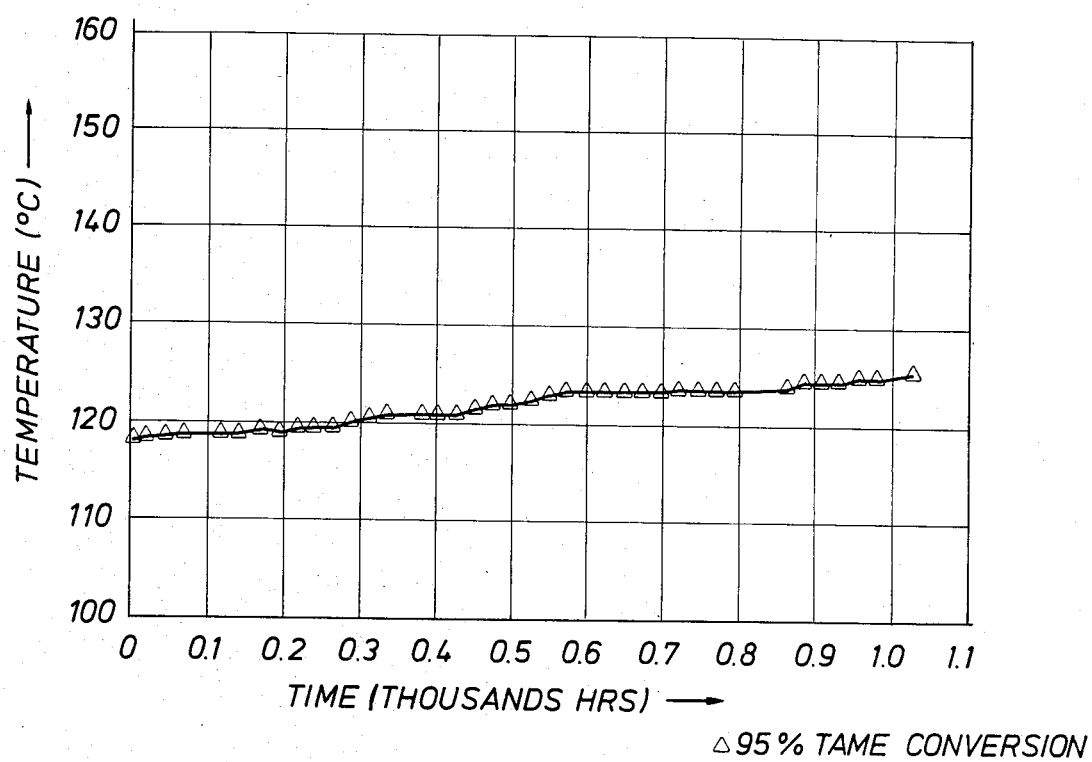
FIG.2A TAME CRACKING CATALYST LIFE TEST
(HF TREATED MONTMORILLONITE)
△ 95% TAME CONVERSION
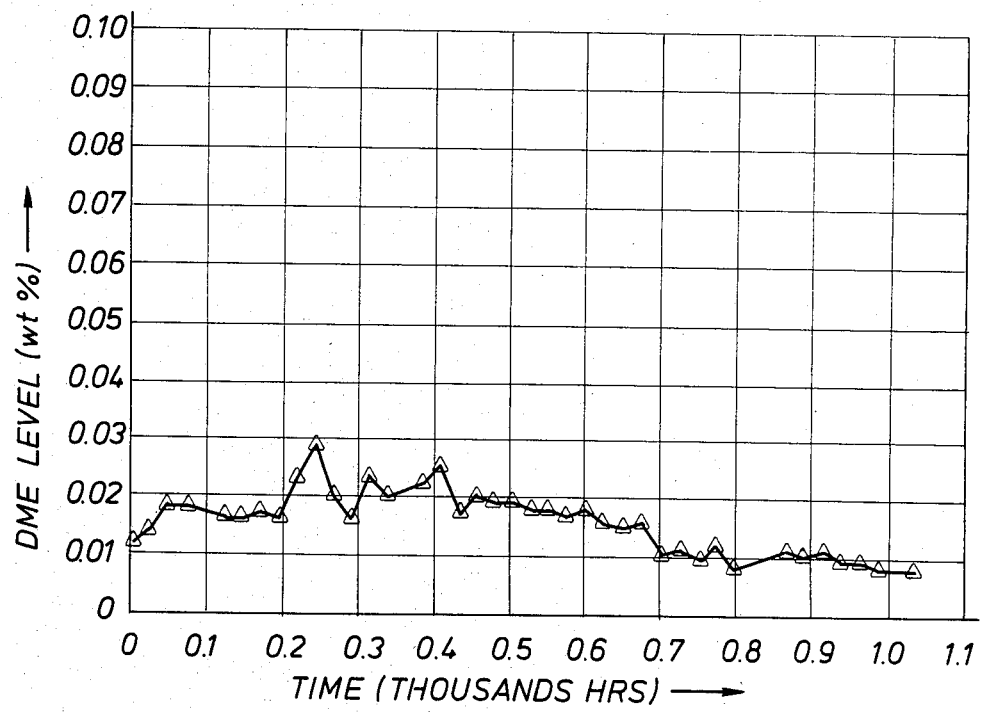
FIG.2B DME LEVEL IN CRACKER PRODUCT
(HF TREATED MONTMORILLONITE)

PRODUCTION OF TERTIARY OLEFINS

FIELD OF THE INVENTION

The present invention relates to a method for the production of tertiary olefins. More particularly, it relates to a method for the production of pure tertiary olefins by the decomposition of alkyl tert-alkyl ethers in the presence of new and improved catalysts.

BACKGROUND OF THE INVENTION

Tertiary olefins are in general commercially produced by the sulfuric acid extraction of such olefins from mixtures containing them obtained e.g., by steam cracking of petroleum feeds. Since this method uses sulfuric acid of high concentrations, the use of expensive materials for the apparatus is essential. Also, dilution of the acid to promote olefin recovery and reconcentrating the acid prior to recycling are required and are expensive. In addition this method is not always advantageous industrially, because tertiary olefins cause side reactions such as polymerization, hydration and the like during extraction with concentrated sulfuric acid.

It is also known that tertiary olefins may be prepared by reacting them selectively from such feeds with a primary alcohol in the presence of an acid catalyst to produce the corresponding alkyl tert-alkyl ethers. Only the tert-alkyl ethers are formed since the secondary olefins react very slowly and the primary olefins are completely inert. Such alkyl tert-alkyl ethers may then be easily separated and subsequently decomposed back to the tertiary olefins and the primary alcohol.

For producing tertiary olefins from alkyl tert-alkyl ethers, there have been proposed methods using various catalysts: For example aluminum compounds supported on silica or other carriers (U.S. Pat. No. 4,398,051). phosphoric acid on various supports (U.S. Pat. No. 4,320,232), metal containing weakly acidic components on a carrier of >20 $M^2$/gm surface area (British Pat. No. 1,173,128). In addition inferior results are disclosed as being obtained utilizing carriers alone in the decomposition of methyl tertiary butyl ether (U.S. Pat. No. 4,398,051) and utilizing $H_2SO_4$ treated clay in the decomposition of t-alkyl ether-alkanols (U.S. Pat. No. 4,254,290).

All these processes suffer from disadvantages. The most important disadvantages arise from the fact that appreciable amounts of dialkyl ether by-product are produced from the primary alcohol. This by-product is wasteful of primary alcohol feed since the dialkyl ether cannot be recovered and decomposed back to primary alcohol for recycle. Also, it causes considerable losses of tertiary olefin product in the final distillation due to the difficulty of separating the dialkyl ether from the tertiary olefin. For example an increase from 100 ppm to 1000 ppm by-product dialkyl ether formation causes substantial increases in olefin losses or capital costs for additional distillation facilities.

Other disadvantages are that the known catalysts do not have good catalysts life in that higher and higher temperatures which eventually become limiting are required to maintain high conversion of the alkyl tert-alkyl ethers. Additionally, larger amounts of the dialkyl ether by-product are produced as the catalyst ages with the disadvantage indicated above. This lack of good catalyst life may be due to the instability of the catalyst, to high temperature being required for good conversion thus promoting fouling, to the catalyst itself promoting fouling or to any or all of these. Also, a number of the catalysts such as resins cannot be regenerated after use.

SUMMARY OF THE INVENTION

According to the invention it has now been discovered that high purity tertiary olefins are obtainable in extremely high yields over a sustained period by bringing alkyl tert-alkyl ethers into contact with a specified catalyst. Specifically, the catalysts of the present invention are clays treated with hydrofluoric acid and/or hydrochloric acid, preferably hydrofluoric acid.

BRIEF DESCRIPTION OF THE DRAWINGS

FIG. 1-A is a graph of dimethylether (DME) in a reactor product of a function of time for two catalysts, one of which is HF treated and one of which is not.

FIG. 1-B is a graph of reactor outlet temperature or a function of time.

FIG. 2-A is a graph of tertiary amylmethyl ether (TAME) cracking (at a 95% conversion) as a function of time.

FIG. 2-B is a graph of DME level in a reactor product or a function of time.

DETAILED DESCRIPTION OF THE INVENTION

The catalysts utilized in the present invention are prepared by reacting a naturally occurring or synthetic clay with HF or HCl followed by calcining. The reacting or incorporation of the HF of HCL with the clay can be accomplished by any means such as contacting the clay with anhydrous HF or HCl gas or by impregnation of the clay with the aqueous acid (e.g., mixing method equilibrium adsorption method, evaporation-to-dryness method, spraying method).

Preferably the clay is reacted with 1.0 to 70 wt %, preferably 20 to 50 wt % hydrofluoric acid or 1.0 to 37%, preferably 20 to 30 wt % hydrochloric acid at temperatures of 0° C. to 50° C., preferably 10° C. to 30° C. for 30 to 120 minutes. The amount of the acid is 0.001 to 1.0 preferably 0.01 to 0.10 grams anhydrous acid/gram clay. Following reaction the fluid is decanted and the clay is then preferably washed first with water and then with alcohol before calcining.

The calcining temperature is selected so as to achieve a highly active high surface area catalyst of a moisture content of less than 5% by wt. Preferably temperatures are 250° to 1000° C., more preferably 400° to 700° C.

The calcination is generally carried out in air, but an atmosphere of an inert gas (e.g. nitrogen, carbon dioxide, argon), steam or mixtures thereof may also be used.

The time for calcination is generally 0.1 to 24 hours, preferably 0.5 to 10 hours, although it depends upon the calcination temperature. The amount of the fluorine or chlorine compound supported on the carrier is 0.1 to 100 parts by weight of the carrier preferably 1.5% to 6.0%.

As examples of the carrier containing silicon oxides used in the present invention, there may be mentioned minerals such as silica, montmorillonite, kaolinite, attapulgite, bentoninte and acid clay. Besides these, silica-alumina, silica-zirconia, silica-magnesia and their mixtures may also be used. Silica may be used in either the form of gel or sol. A particularly preferred carrier is one prepared from attapulgite or montmorillonite type minerals. The surface area of the carrier is not particularly limiting, but preferably, it is more than 1 $m^2$/g, more preferably above 40 m²/gm. Preferred surface areas after calcination are in the range of 100 m²/gm to 400 m²/gm.

The performance of the catalyst used in the present invention is superior in activity and selectivity to any of the catalysts described above. Although details are not clear this may be because of the unique mixture of acids and basic sites affordable by these materials. In addition, the catalyst of this invention provides extended catalytic life which is highly important for industrial use.

The extended catalyst life in the present invention process is due at least in part to the high stability of HF or HCl treated clay as opposed to other acid treated clays. Thus, it is known that acids such as $H_2SO_4$ and $H_3PO_4$ in the presence of components such as alcohols form esters which under the reaction conditions are volatile thereby changing the acidity of the catalyst as it ages. The HF and HCl treated clays have essentially the same halide level before and after use.

The reaction of decompositon of the tert-alkyl ethers takes place with good yields under atmospheric pressures, but it is preferred to operate under slightly superatmospheric pressures so as to permit the use of cooling water without any other expedient to carry out the condensation of the products which are obtained.

The working pressures are generally ranging from 1 to 20 kilograms/sq.cms absolute; preferably under a pressure which is at least equal to the vapor pressure of the described olefin at the condenstion temperature which is foreseen.

The reaction is carried out at a temperature below 250° C., in the range 100°–250° C. and preferably in the range from 110° to 230° C. The reaction is carried out at a spatial velocity, as expressed in terms of volume of liquid per volume of catalyst per hour (LHSV) ranging between 0.5 and 30, preferably in the range 1 to 5. Preferably also conditions are selected to obtain conversions of the tert-alkyl ethers above 80% preferable above 90%.

The primary alcohols used which can be recovered on completion of the decomposition reaction preferably contain from 1 to 6 carbon atoms, more preferably 1 to 5 carbon atoms, most preferably methanol.

The method according to the present invention can be employed for the recovery of tertiary olefins from mixtures of $C_4$ to $C_7$ olefins, such as, for example, those coming from the thermal cracking, steam cracking or catalytic cracking of petroleum feedstocks.

Among the several tertiary olefins which can be obtained in a pure state there can be listed isobutylene from $C_4$ monoolefin fractions, isoamylenes such as 2-methyl-2-butene and 2-methyl-1-butene from $C_5$ monoolefin fractions, the isohexenes such as 2,3-dimethyl-1-butene, 2-3-dimethyl-2-butene, 2-methyl-1-pentene, 2-methyl-2-pentene, 3-methyl-2-pentene (cis and trans), 2-ethyl-1-butene and 1-methylcyclopentene from $C_6$ monoolefin fractions, or, lastly, the tertiary isoheptenes from $C_7$ monoolefin fractions.

The conversion of the tert-alkyl ether into primary alcohol and tertiary olefin is virtually quantitative. No formation of dimers and trimers of the recovered tertiary olefin is experienced and no tertiary alcohol is likewise formed.

The present invention will be illustrated in more detail with reference to the following examples, which are not however to be interpreted as limiting the scope of the invention.

EXAMPLE 1

A preferred hydrofluoric acid treated clay catalyst of this invention was prepared as follows: 250 gm of attapulgite clay commercially available from Engelhard Corporation was introduced into a plastic vessel containing 450 gm of deionized water, 50 gm of 50% hydrofluoric acid solution was added with stirring. The mixture was allowed to stand for 1 hour with occasional stirring and then the water layer was decanted into caustic solution containing ice. 500 gm of deionized water was added to the solids layer and decanted followed by 500 gm of methanol and decanting. The final solids layer was dried in a vacuum oven at 150° C. and the dried solids were then calcined at 500° C. for 2 hours to prepare the final catalyst. Such catalyst had the following characteristics: surface area 160 m²/gm, of 4.5 wt %, pore volume 0.60 cc/gm, bulk density 0.58 gm/cc, moisture content <3.0%.

EXAMPLE 2

A continuous 1000 hour test to determine results obtained in a catalyst run length test was conducted utilizing a catalyst prepared as described in Example 1 and also for comparison a catalyst prepared using the same attapulgus clay without an HF acid treating step. The latter catalyst was calcined at 500° C. with air for 21 hours and had the following characteristics: surface area 156 m²/gm, pore volume 0.60 cc/gm, bulk density 0.58 gm/cc, moisture content <3.0%.

Separate life tests with the two catalysts were run in a continuous laboratory unit. In this unit tertiary amyl methyl ether (TAME) feed prepared from steam cracking product was pumped out of a feed reservoir using a metering pump.

Typical TAME feed analyses taken at three times during the run were as follows:

| TAME Feed Analyses | | | |
|---|---|---|---|
| | wt % | | |
| Component | A | B | C |
| Methanol | 0.127 | 0.111 | 0.172 |
| C5's (hydrocarbon) | 0.310 | 0.310 | 0.177 |
| C6's (hydrocarbon) | 1.750 | 2.118 | 1.076 |
| TAME | 94.35 | 94.51 | 96.56 |
| Tert.Amyl Alcohol | <1.3 | 0.542 | 0.421 |
| Isoprene Ethers | 0.037 | 0.041 | 0.024 |
| Pentadiene Ethers | 0.290 | 0.213 | 0.082 |
| n-Heptane | 1.300 | 1.327 | 0.271 |
| Unknown Unsat C6 Ether | — | — | 0.085 |

The TAME was vaporized and superheated in a 12" long ½" OD (0.41" ID) tube wrapped with electrical heating tape. The effluent from the preheater then entered the reactor which was a ¾" OD (0.61" ID) tube packed with catalyst in a Lindberg furnace having a 12" long heating zone. The surface temperature of the heating element was controlled and the process temperature out of the catalyst bed monitored with thermocouple placed about ¼" to ½" above the catalyst bed. The reactor was configured for upflow. The reactor effluent was condensed with chilled water (10°–15° C.) and collected. The reactor pressure was set with a back-pressure regulator located between the product condenser and the product receiver.

The reactor was loaded with about 57 cm³ of the two catalysts (38.6 grams), the packed bed depth being about 28.5 cm. The feed pump was set for a feed rate of about 105 cc/hr, which corresponds to an LHSV=1.85$^{-1}$. The back-pressure regulator on the reactor was set at 100 K Pa. The preheater process outlet temperature was typically 180°-190° C., and the cracker process outlet temperature was controlled to maintain 95% TAME disappearance. FIG. 1-A shows the dimethyl ether (DME) make vs. time online FIG. 1-B shows the cracker process outlet temperature vs. time online. As the FIG. 1-B shows, the temperature started at 130° C. and was raised through the run to maintain the conversion because the catalyst was fouling. The HF treated clay was analyzed at the conclusion of the run and found to have the same fluorine content as at the beginning of the run (when corrected for the carbon lay down).

This example shows that the HF treated clay is superior both in providing lower DME make and in the temperature required for 95% conversion. Also, it is stable in that no fluorine content is lost.

EXAMPLE 3

A tertiary amylmethyl ether (TAME) cracking experiment was performed in an identical fashion as described in Example 2 using Harshaw/Filtrol Grade 62 montmorillonite 3/16" extrudates. After calcination 500° C. in air for four hours, the catalyst had the following characteristics: Surface area 305 m$^2$/gm, moisture content <3.0%, bulk density 0.68 g./cc.

The reactor temperature was adjusted to maintain 95% TAME dissappearance. The reactor outlet temperature and product analysis was then recorded. The reactor outlet temperature was 142° C. and the DME make was 1000 ppm over the 40 hour run length at 95% TAME disappearance. This run shows the poor results obtained with montmorillonite not especially acid treated as described in this invention.

EXAMPLE 4

A sample of Harshaw/Filtrol Grade 62, montmorillonite 3/16" extrudates were hydrofluoric acid treated as described in Example 1 except that the methanol washing step was deleted. After calcination at 500° C. in air for four hours the catalyst had the following characteristics: Surface area 305 m$^2$/gm, % Fluorine 2.1%, Pore volume 0.56, % moisture <3.0% Bulk density 0.62 g./cc.

Exactly as in Example 2, a life test was performed on this catalyst. The reactor temperature was adjusted to maintain 95% TAME disappearance. The results depicted in attached FIG. 2 were obtained over the 1000 hr, life run. FIG. 2-A shows the reactor outlet temperature as a function of time. FIG. 2-B shows the percentage of DME in the reactor outlet as a function of time. This run shows the good results obtained with this catalyst.

EXAMPLE 5

Following the procedure described in Example 2 the following Aluminas were evaluated as TAME decomposition catalysts.

| Alumina | Temp @ 95% TAME Disappearance | DME yield (WT %) |
| --- | --- | --- |
| AL 3996E (Harshaw) | >200° C. | >1 |
| P-0620T (Harshaw) | 195° C. | >0.2 |
| AL 3996R (Harshaw) | 210° C. | >2.3 |
| AL 4912E (Harshaw) | 160° C. | 0.5 |

As can be seen none of these materials are comparable to the catalysts of this invention in terms of process outlet temperature or DME yield.

EXAMPLE 6

Following the procedure described in Example 2 the following ion exchange resin catalysts were evaluated as TAME decomposition catalysts.

| Resin | Temp @95% TAME disappearance | DME yield WT % |
| --- | --- | --- |
| Rohm & Haas Amberlyst 15 ® H+ form | 115–120° C. | 2.0 |
| Amberylst 15 Cs exchanged | 135–140° C. | 0.15 |
| Amberylst 15 Zn exchanged | 140–145° C. | 0.10 |

As can be seen none of the resin catalysts are comparable in performance to the catalysts of this invention. Additionally, these resin materials have the disadvantage that they cannot be easily regenerated (air or steam air decoked) as can the catalysts of this invention.

EXAMPLE 7

Raw Pumice was hydrofluoric acid treated as in Example 1. The catalyst was calcined in air for 4 hours at 500° C. and then tested for TAME cracking as in Example 2. The process outlet temperature for 95% TAME disappearance was 175° C. and the DME yield was greater than 1500 ppm. This performance is attributed to the very low surface area of this catalyst which was measured to be 1.3 m$^2$/gm.

What is claimed is:

1. A process for the preparation of tertiary olefins starting from the corresponding tertiary ethers, consisting in contacting said tertiary ether at a temperature of from 100° C. to 250° C. with a catalyst prepared by reacting a clay with HF and/or HCl followed by calcining, to form said tertiary olefin.

2. The process of claim 1 in which the clay is a natural clay.

3. The process of claim 1 in which the clay is attapulgus clay.

4. The process of claim 1 in which the clay is montmorillonite clay.

5. A process for the preparation of C$_4$-C$_7$ tertiary monoolefins starting from the corresponding tertiary ethers, consisting in contacting said tertiary ether at a temperature of from 100° C. to 250° C. with a catalyst prepared by reacting a clay with an acid selected from the group consisting of 10–70 wt % hydrofluoric acid, 10 to 37 wt % hydrochloric acid and mixtures thereof, followed by drying and calcining, to form said tertiary monoolefin.

6. The process of claim 5 in which the acid is hydrofluoric acid.

7. The process of claim 5 in which the clay is attapulgus clay.

8. The process of claim 6 in which the clay is montmorillonite clay.

9. The process of claim 5 in which the tertiary ethers are C$_5$ ethers.

10. The process of claim 9 in which the acid is hydrofluoric acid.

11. The process of claim 5 in which the catalyst has a surface area of above 40M$^2$/gm.

12. The process of claim 11 in which the LHSV is 0.5. to 30 and conditions are selected to obtain conversions of the tertiary ethers of above 80%.

* * * * *